United States Patent [19]
Caizza et al.

[11] Patent Number: 5,738,665
[45] Date of Patent: Apr. 14, 1998

[54] SHIELD AND ACTUATOR FOR NEEDLES

[75] Inventors: Richard J. Caizza, Barry Lakes, N.J.; Bronwen Walters, Dania, Fla.

[73] Assignee: Becton, Dickinson and Company, FranklinLakes, N.J.

[21] Appl. No.: 721,512

[22] Filed: Sep. 26, 1996

[51] Int. Cl.⁶ .................................................. A61M 5/00
[52] U.S. Cl. .................................. 604/263; 604/192
[58] Field of Search ...................... 604/263, 192, 604/198, 187

[56] References Cited

U.S. PATENT DOCUMENTS

| | | | |
|---|---|---|---|
| 3,840,008 | 10/1974 | Noiles | 128/221 |
| 4,735,618 | 4/1988 | Hagen | 604/192 |
| 4,790,828 | 12/1988 | Dombrowski et al. | 604/198 |
| 4,795,443 | 1/1989 | Permenter et al. | 604/198 |
| 4,820,277 | 4/1989 | Norelli | 604/192 |
| 4,826,490 | 5/1989 | Byrne et al. | 604/198 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,886,503 | 12/1989 | Miller | 604/192 |
| 4,887,998 | 12/1989 | Martin et al. | 604/110 |
| 4,898,589 | 2/1990 | Dolgin et al. | 604/198 |
| 4,904,244 | 2/1990 | Harsh et al. | 604/187 |
| 4,911,706 | 3/1990 | Levitt | 604/198 |
| 4,950,250 | 8/1990 | Haber et al. | 604/192 |
| 5,092,851 | 3/1992 | Ragner | 604/192 |
| 5,108,379 | 4/1992 | Dolgin et al. | 604/198 |
| 5,242,417 | 9/1993 | Paudler | 604/192 |
| 5,348,544 | 9/1994 | Sweeney et al. | 604/192 |

*Primary Examiner*—John D. Yasko
*Attorney, Agent, or Firm*—John L. Voellmicke

[57] ABSTRACT

A shieldable needle assembly includes a needle guard slidably movable along a needle cannula from a proximal position where the distal end of the needle cannula is exposed to a distal position where the distal end of the needle cannula is safely shielded within the needle guard. A hinged arm assembly connects the needle guard assembly to needle hub. A trigger is articulated to the needle hub at a location proximally of the hinged arm. Distally directed digital forces cause the trigger to rotate such that the trigger urges the hinged arm from a collapsed condition to an extended condition.

15 Claims, 5 Drawing Sheets

SHIELD AND ACTUATOR FOR NEEDLES

FIELD OF THE INVENTION

The subject invention relates to safety shields for preventing accidental sticks with sharp medical implements.

DESCRIPTION OF THE PRIOR ART

An accidental stick with a used needle cannula can transmit disease. As a result, most prior art needle cannulas are used with a safety shield for preventing accidental sticks.

A shieldable needle assembly is taught in U.S. Pat. No. 5,348,544. This prior art needle assembly includes a needle cannula having a proximal end and a pointed distal end. Portions of the needle cannula adjacent its proximal end are securely retained in a needle hub. The needle hub is releasably threadedly engaged with a luer collar on a syringe.

The prior art shieldable needle assembly includes a needle guard which is slidably movable along the needle cannula from a proximal position substantially adjacent the hub to a distal position surrounding the distal end of the needle cannula. The needle guard includes a plastic cap configured for sliding along the needle cannula and a metallic clip secured in the cap and biased against needle cannula as the cap is moved in a distal direction. However, once clip passes distally beyond the needle cannula, it will resiliently move toward an unbiased condition to protectively cover the distal end of the needle cannula.

The prior art needle assembly further includes a hinged arm assembly for initiating movement of the needle guard and for controlling the amount of movement of the needle guard along the needle cannula. The hinged arm assembly includes a proximal segment hingedly connected to the needle hub and a distal segment articulated to portions of the proximal segment remote from the hub. The distal segment of the hinged arm assembly is further articulated to the needle guard.

In the collapsed needle exposing condition the needle guard is substantially adjacent to the hub. However, distally directed digital forces may be exerted on the hinged arm assembly to urge the hinged arm assembly into an extended condition in which its segments are substantially linearly arrayed and generally parallel to the needle cannula. This extension of the hinged arm assembly will generate sliding distal movement of the needle guard along the needle cannula. The dimensions of segments of the hinged arm assembly are selected to permit distal portions of the needle guard to move beyond the distal end of the needle cannula and to prevent proximal portions of the needle guard from moving beyond the distal end of needle cannula.

Movement of hinged arm assembly from the collapsed condition to the extended condition is facilitated by a biased hinge intended to propel the needle guard distally. Thus, the user of the prior art shieldable needle assembly need not push the hinged arm assembly entirely into the extended condition.

There is a desire to make further improvements over the prior art shieldable needle assembly described in U.S. Pat. No. 5,348,544. For example, it is desired to provide a more visually apparent actuation structure for unmistakable encouraging the single handed-single digit actuation for which the needle shield assembly is designed. It is further desired to permit actuation with even a shorter stroke of movement of the user's finger. This latter objective is desirable in that it facilitates easier actuation of the shield.

SUMMARY OF THE INVENTION

The subject invention is directed to an easily shieldable needle assembly. The assembly includes a needle having a proximal end and a pointed distal end. The proximal end of the needle may be securely mounted in a needle hub, which in turn may be mounted releasably on a hypodermic syringe or other medical implement. The assembly further includes a needle guard that is slidably movable along the needle cannula from a proximal position where the distal end of the needle is exposed, to a distal position where the distal end of the needle is safely shielded by the needle guard. The needle guard may include a plastic cap and a metallic clip. The clip may be securely retained between the cap and the needle, and may be configured for slidable engagement with the needle as the guard moves toward its distal position. However, portions of the clip are configured to protectively cover the pointed distal end of the needle after sufficient distal movement of the needle guard.

The shieldable needle assembly of the subject invention further includes a hinged arm assembly connecting the needle guard with structure spaced proximally from the distal end of the needle. For example, the hinged arm assembly may include a proximal segment articulated to structure near the proximal end of the needle and a distal segment articulated to the needle guard. The proximal and distal segments of the hinged arm assembly may be articulated to one another and may include biasing means for selectively urging the needle guard toward its distal position. The biasing means may be stable in both the proximal position of the needle guard and in the distal position thereof, such that the biasing means is not pre-stressed in either of these extreme positions of the hinged arm assembly. The hinged arm assembly is dimensioned to permit the needle guard to protectively shield the pointed distal end of the needle when the hinged arm assembly is extended. However, these dimensions also prevent the needle guard from moving distally beyond the needle.

The shieldable needle assembly further includes a trigger articulated to a location proximally of the hinged arm assembly. The trigger includes an actuating surface dimensioned and configured for convenient digital activation by a thumb or forefinger of the hand holding the medical implement to which the shieldable needle assembly is connected. The trigger further may include a cam edge or cam surface for engaging portions of the hinged arm assembly and urging the hinged arm assembly from the collapsed condition into the extended condition. The trigger may be dimensioned, configured, textured and/or colored to be clearly distinguishable from other portions of the shieldable needle assembly and to provide a clear indication of its intended function.

In use, distally directed digital forces may be exerted on the actuating surface of the trigger to cause the trigger to rotate about its hinged connection. These digital forces will cause the cam surface or edge of the trigger to engage proximally facing surfaces of the hinged arm assembly and to cause the hinged arm assembly to quickly move from its collapsed condition into its extended position. The trigger may be configured to ensure that camming forces are exerted throughout the range of movement of the hinged arm assembly. Alternatively, the cam may merely urge the hinged arm assembly into a position where the spring means will urge the hinged arm assembly into the extended position without the benefit of continued pressure by the cam of the trigger. In other embodiments, movement of the hinged arm assembly from the collapsed to the extended condition may be attributable to a combination of spring forces and digital forces transmitted through the trigger.

The trigger can provide an enhanced mechanical advantage, and hence easier actuation, while also providing a clearer indication of preferred operation of the shieldable needle assembly.

DETAILED DESCRIPTION OF THE PREFERRED EMBODIMENT

Figure 1:
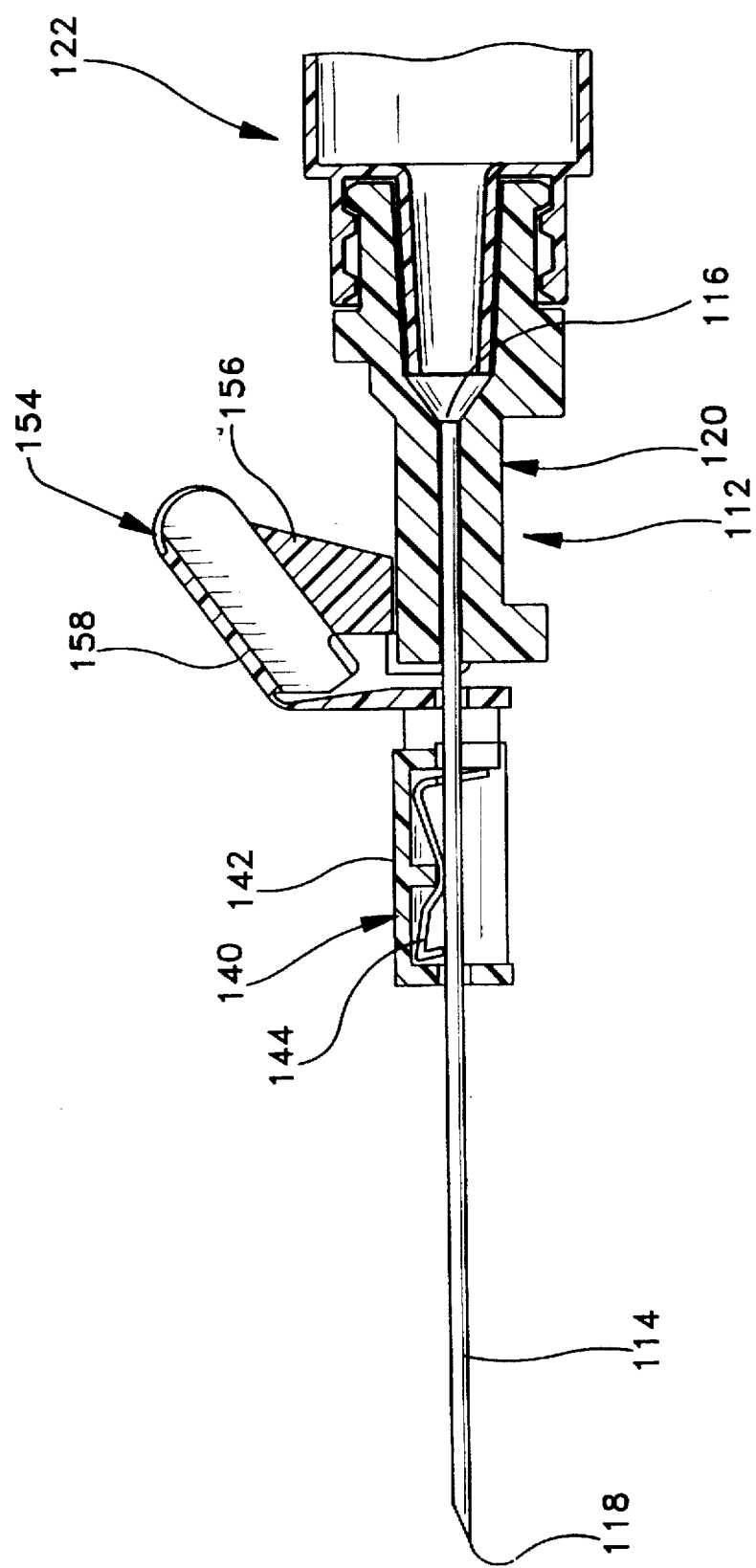
FIG. 1 is a side elevational view of a prior art shieldable needle assembly.

While this invention is satisfied by embodiments in many different forms, there is shown in the drawings and will be herein described in detail a preferred embodiment of the invention with the understanding that the present disclosure is to be considered exemplary of the principles of the invention and is not intended to limit the scope of the invention to the embodiment illustrated. The scope of the invention will be measured by the appended claims and their equivalents.

Adverting to FIG. 1, a needle shield assembly 112 includes a needle guard 140 which is slidably movable along needle cannula 114 from a proximal position substantially adjacent to hub 120 to a distal position surrounding distal end 118 of needle cannula 114. The needle shield assembly is connected to syringe 122. Needle guard 140 includes a plastic cap 142 configured for sliding along the needle cannula. Needle guard 140 further includes a metallic clip 144 secured in cap 142 and biased against the needle cannula as cap 142 is moved in a distal direction. When clip 144 passes distally beyond needle cannula 114, the clip will resiliantly move toward an unbiased condition to protectively cover distal end 118 of the needle cannula.

The prior needle assembly further includes a hinged arm assembly 154 for initiating movement of needle guard 144 and for controlling the amount of movement of the needle guard along the cannula. Hinged arm assembly 154 includes a proximal segment 156 hingedly connected to the needle hub and the distal segment 158 articulated to portions of the proximal segment 156 remote from hub 120. Distal segment 158 of the hinged arm assembly is further articulated to the needle guard.

FIG. 1 shows the prior art hinged arm assembly 154 in a collapsed condition such that needle guard 140 is substantially adjacent to hub 120. However, distally directed digital forces may be exerted on hinged arm assembly 154 to urge the hinged arm assembly into an extended position in which segments 156 and 158 are substantially linearly arrayed and generally parallel to the needle cannula. The extension of hinged arm assembly 154 will generate sliding distal movement of needle guard 140 along the needle cannula. The dimensions of segments 156 and 158 of the hinged arm assembly are selected to permit distal portions of needle guard 140 to move beyond distal end 118 of the needle cannula and to prevent proximal portions of needle guard 140 for moving beyond distal end 118 of needle cannula.

Movement of hinged arm assembly 154 from the collapsed condition, illustrated in FIG. 1, to the extended position is facilitated by a biasing hinge intended to propel the needle guard distally. Thus, the user of the prior art needle shield assembly need not push the hinged arm assembly 154 entirely into the extended position.

A shieldable needle assembly in accordance with the subject invention is identified generally by the numeral 12 in FIGS. 2–6. Shieldable needle assembly 12 includes a needle cannula 14 having opposed proximal and distal ends 16 and 18 and a lumen extending continuously therebetween. Proximal end 16 of needle cannula 14 is securely embedded in a unitarily molded thermoplastic hub 20. Hub 20 is configured for releasable connection to a hypodermic syringe 22.

Syringe 22 includes a tubular syringe barrel 24 having a proximal end (not shown), an opposed distal end 28 and a fluid receiving chamber 30. Tip 34 projects distally from distal end 28 of syringe barrel 24 and includes a passage 36 extending therethrough for communication with chamber 30. A generally cylindrical luer collar 38 concentrically surrounds tip 34 and includes an array of threads for releasable engagement with projections on hub 20 of shieldable needle assembly 12.

Shieldable needle assembly 12 further includes a needle guard assembly 40 having a cap 42 and a clip 44 which is preferably metallic. Cap 42 includes opposed proximal and distal end walls 46 and 48 and a chamber 50 therebetween. Proximal and distal end walls 46 and 48 each include a needle receiving aperture therethrough such that cap 42 can be slidably engaged over needle cannula 14. Thus, cap 42 can be slidably moved from a proximal position substantially adjacent needle hub 20 to a distal position where cap 42 substantially surrounds and encloses distal tip 18 of needle cannula 14.

Metallic clip 44 of needle guard assembly 40 includes a proximal leg 52 with an aperture through which needle cannula 14 extends. Metallic clip 44 further includes a distal leg 53 bent to be substantially orthogonal to needle cannula 14. Portions of metallic clip 44 between proximal and distal legs 52 and 53 are resiliently deflected such that distal leg 53 is biased against the exterior of needle cannula 14. Thus, clip 44 will slide with cap 42 along needle cannula 14. Portions of metallic clip 44 between the proximal and distal legs thereof are configured to bias the distal leg of metallic clip 44 against needle cannula 14. Thus, distal leg 53 of metallic clip 44 will slide against needle cannula 14 as needle guard assembly 40 is slidably advanced from its proximal position shown in FIG. 2 to its distal position shown in FIG. 5. However, after sufficient distal movement, distal leg 53 of clip 44 will advance beyond distal end 18 of needle cannula 14. Metallic clip 44 will then resiliently return toward an undeflected or less deflected condition in which distal leg 53 protectively covers distal end 18 of needle cannula 14. Thus, metallic clip 44 will prevent a proximal movement of needle guard assembly 40 that could re-expose tip 18 of needle cannula 14.

Shieldable needle assembly 12 further includes a hinged arm assembly 54 having a proximal segment 56 and a distal segment 58. Proximal segment 56 of hinged arm assembly 54 has a proximal end articulated to needle hub 20 and a distal end articulated to the proximal end of distal segment 58. Distal segment 58 of hinged arm assembly 54 is further articulated to needle guard assembly 40. The articulation between proximal segment 56 and hub 20 may be by a spring hinge, such as the over center hinge shown in U.S. Pat. No. 5,348,544. Such a hinge develops stored energy during initial stages of opening and then uses that stored energy to complete the opening. The articulation of distal segment 58 of hinged arm assembly 54 to needle guard assembly 40 may include a flexible connection to portions of cap 42 near proximal end wall 46.

Figure 2:
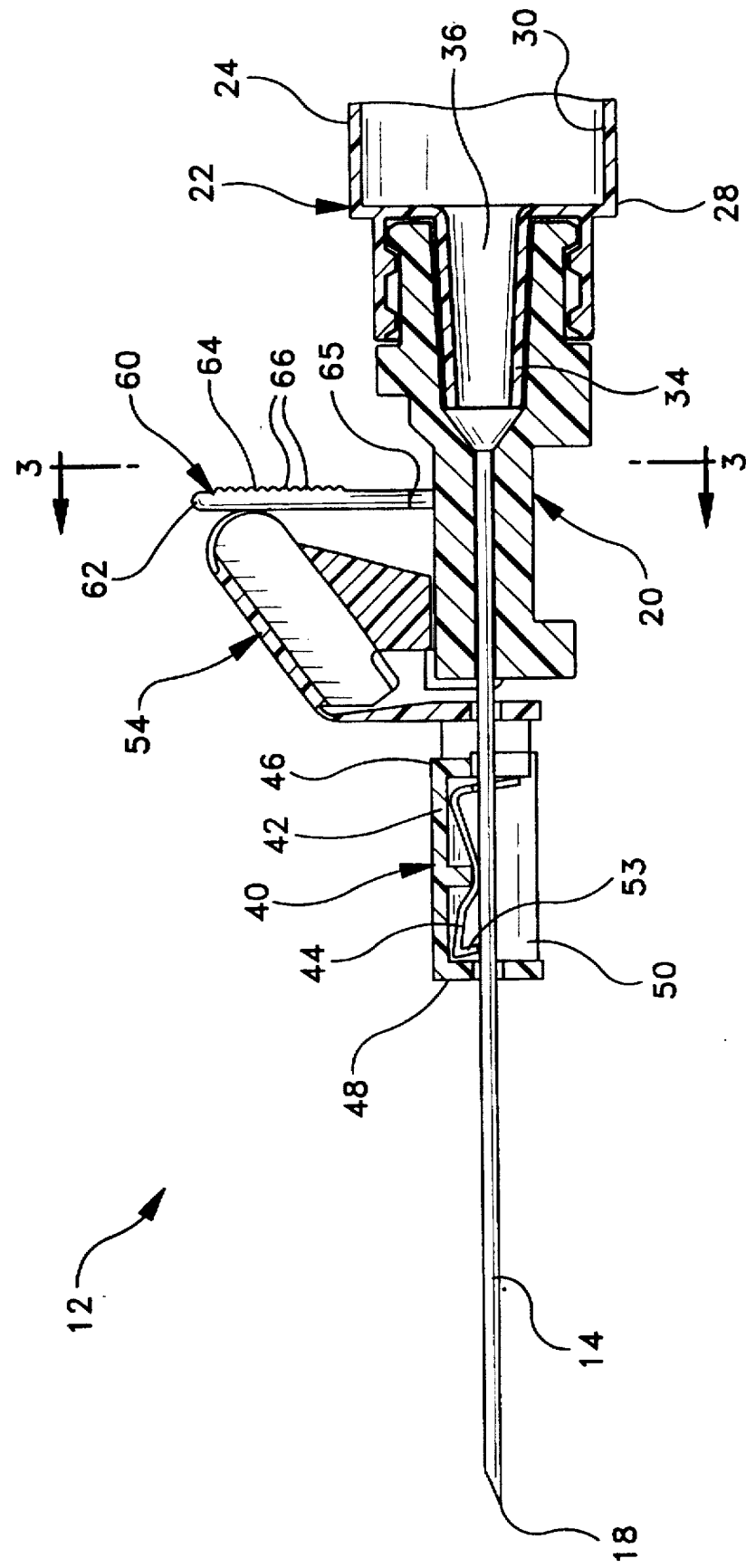
FIG. 2 is a side elevational view of a shieldable needle assembly of the subject invention in a ready-to-use condition.
Figure 3:
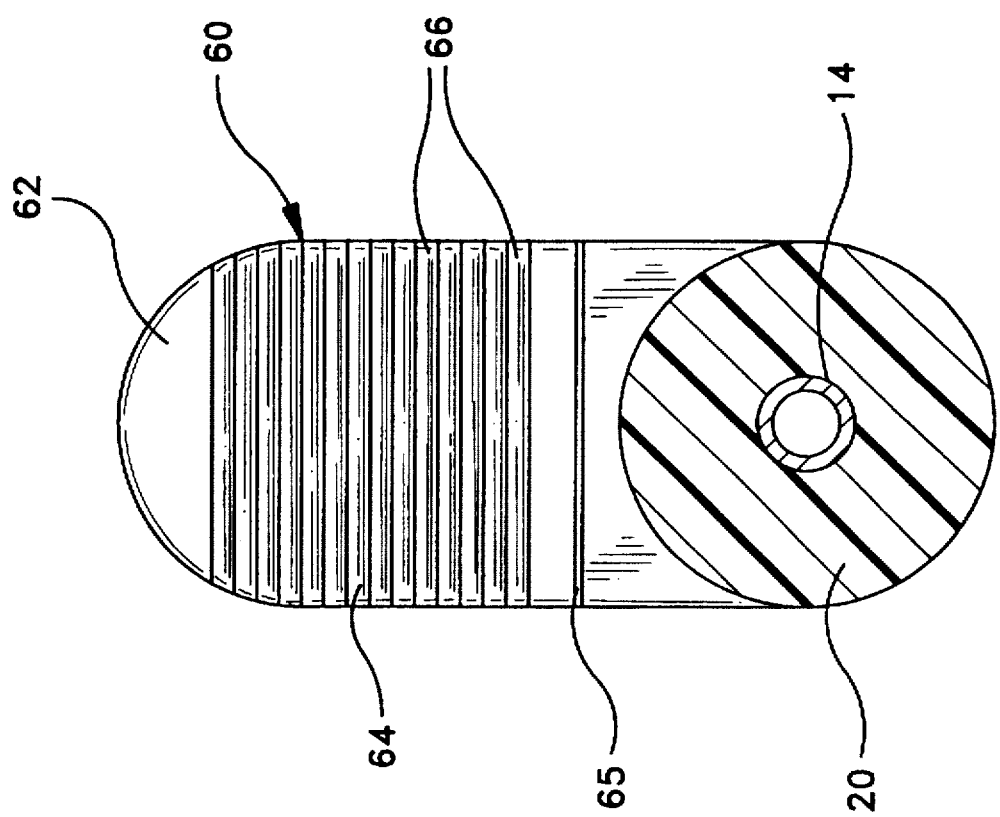
FIG. 3 is a cross-sectional view taken along line 3—3 in FIG. 2.

Hinged arm assembly 54 can be folded into a collapsed condition as shown in FIG. 2 such that needle guard assembly 40 is substantially adjacent hub 20. However, hinged arm assembly 54 can be extended to permit needle guard assembly 40 to slidably advance toward distal end 18 of needle cannula 14. Proximal and distal segments 56 and 58 of hinged arm assembly 54 are dimensioned relative to one another to permit needle guard assembly 40 to slidably advance into surrounding relationship with distal end 18 of needle cannula 14. However advancement of needle guard assembly 40 distally beyond needle cannula 14 is positively presented by hinged arm assembly 54.

Shieldable needle assembly 12 further includes a trigger 60 articulated proximally of articulated arm assembly 54 for rotation about an axis transverse to needle cannula 14, as defined by hinge 65, and substantially parallel to the rotational axes of hinged arm assembly 54. Trigger 60 further includes a preferably convexly shaped, arcuate cam edge 62 at locations thereon remote from the articulated connection to needle hub 20. Additionally, trigger 60 includes an actuating face 64 facing substantially proximally in the articulated position depicted in FIG. 2. Actuating face 64 is preferably a non-planer surface such as a surface having a plurality of ridges 66 for facilitating digital manipulation of trigger 60. Surface irregularities other than ridges 66 may be provided for achieving these purposes.

FIG. 2 shows shieldable needle assembly 12 in its ready-to-use condition. In this condition needle guard assembly 40 is disposed in a proximal position on needle cannula 14 substantially adjacent hub 20. Additionally, in this ready-to-use condition, hinged arm assembly 54 is substantially collapsed such that proximal and distal segments 56 and 58 thereof are adjacent one another. Still further, in this ready-to-use condition shown in FIG. 2, trigger 60 is aligned substantially orthogonal to needle cannula 14 with camming edge 62 of trigger 60 being in abutting contact with portions of hinged arm assembly 54 substantially adjacent the articulation between proximal and distal segments 56 and 58 thereof and, preferably, primarily in contact with the proximal segment.

Shieldable needle assembly 12 is used by exerting distally directed digital pressure on actuating face 64 of trigger 60. Ridges 66 on actuating face 64 prevent the thumb or forefinger exerting the digital pressure from sliding off trigger 60. These distally directed digital forces on trigger 60 cause trigger 60 to rotate about its hinged connection to hub 20 to further cause cam edge 62 of trigger 60 to exert forces on portions of proximal segment 56 of hinged arm assembly 54 remote from hub 20. These forces on proximal segment 56 of hinged arm assembly 54 cause proximal segment 56 to rotate about its hinged connection to hub 20 and further cause hinged arm assembly 54 to move toward an extended condition.

Figure 4:
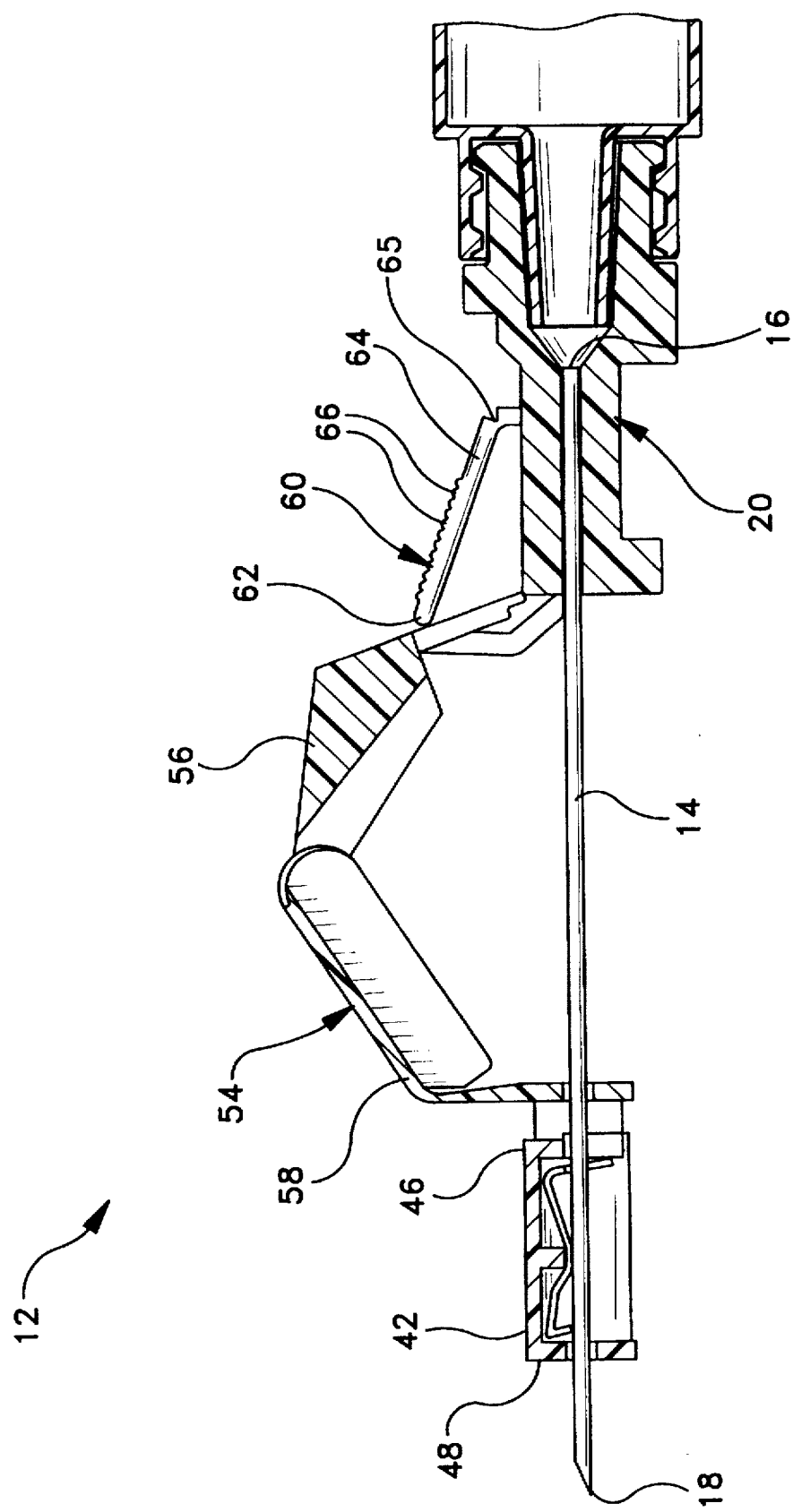
FIG. 4 is a side elevational view similar to FIG. 2, but showing the shieldable needle assembly in an intermediate position.

Needle guard assembly 40 will slidably advance distally along needle cannula 14 as hinged arm assembly 54 is extended, as shown in FIG. 4. Additionally, arcuate cam edge 62 of trigger 60 will slide along proximal segment 56 of hinged arm assembly 54 as both the proximal segment 56 and trigger 60 rotate. Thus, even though the relative orientation of proximal segment 56 of hinged arm assembly 54 changes, continued distally directed forces will be exerted thereon by camming edge 62 of trigger 60.

Figure 5:
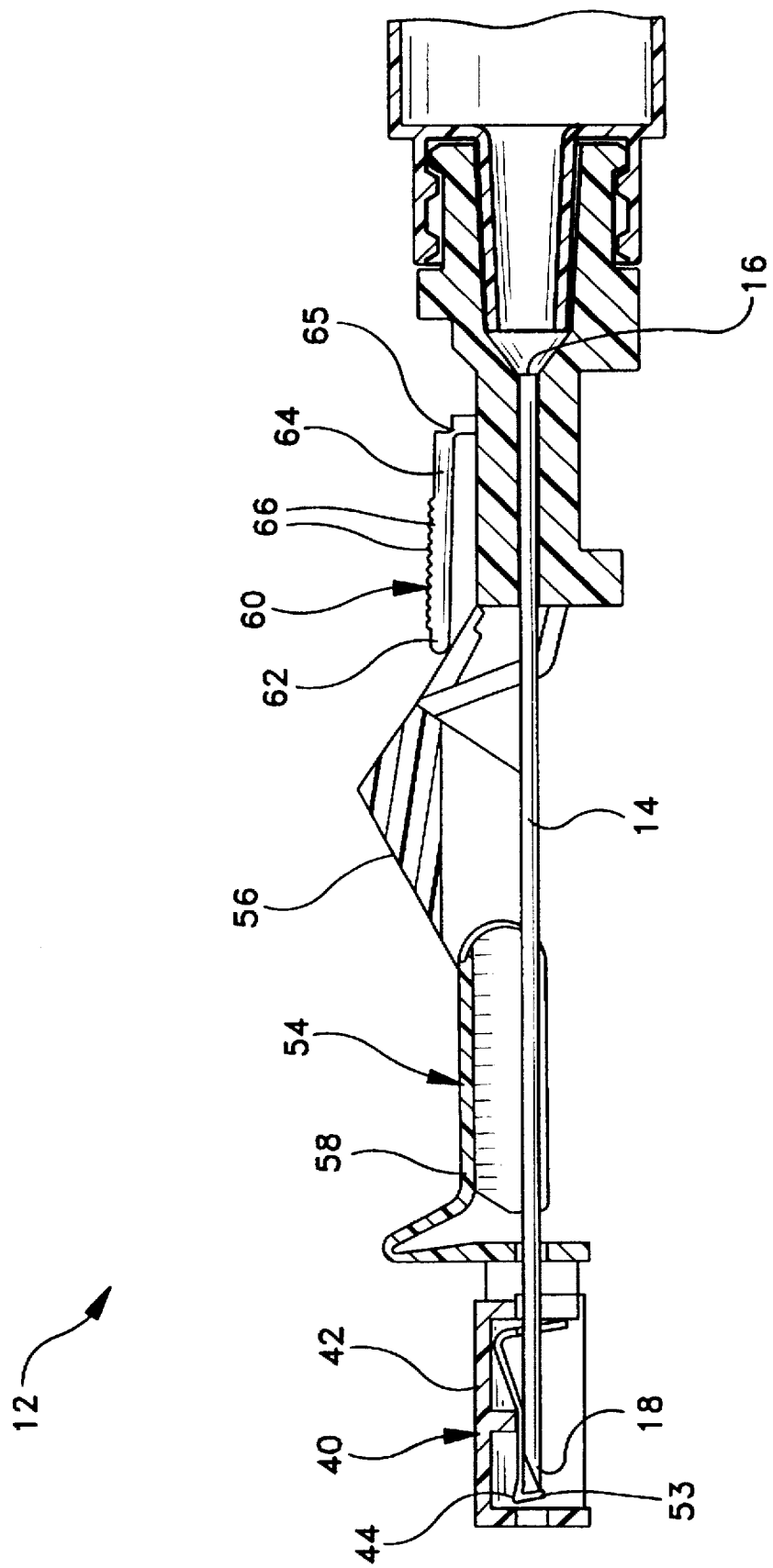
FIG. 5 is a side elevational view similar to FIGS. 2 and 4 but showing the shieldable needle assembly in a fully extended condition for protectively shielding the distal tip of the needle cannula.

Continued distally directed digital forces on trigger 60 will propel needle guard assembly 40 toward distal end 18 of needle cannula 14 and into the shielding position shown in FIG. 5. This propulsion of needle guard assembly 40 distally may be facilitated by biasing forces exerted by the over center hinge connection of proximal segment 56 of hinged arm assembly 54 to hub 20. In the fully extended condition of hinged arm assembly 54, distal leg 53 of metallic clip 44 will have passed beyond distal end 18 of needle cannula 14. Clip 44 then will resiliently return toward an undeflected condition such that distal leg 53 covers distal end 18 of needle cannula 14 to prevent re-exposure of distal end 18. Thus, extended hinged arm assembly 54 will prevent needle guard assembly 40 from moving distally beyond needle cannula 14 and metallic clip 44 will prevent needle guard assembly 40 from moving proximally into a position where distal end 18 of needle cannula 14 may be re-exposed.

Trigger 60 of shieldable needle assembly 12 defines a clearly identifiable location for exertion of the distally directed digital forces. Additionally, trigger 60 enables the distally directed digital forces to be exerted from a location further from distal end 18 of needle cannula 14. The combined effect of continuous distal forces exerted by camming edge 62 of trigger 60 and the biasing effect of the hinged connection between arm assembly 54 and hub 20 enables rapid shielding operation.

What is claimed is:

1. A shieldable needle assembly comprising:

a needle having proximal and distal ends;

a hub securely mounted around said proximal end of said needle;

a needle guard slidably mounted on said needle and movable from a proximal position where said distal end of said needle is exposed to a distal position where said needle guard safely guards said distal end of said needle;

a hinged arm articulated to said hub and to said needle guard and being movable from said collapsed condition where said needle guard is in said proximal position to an extended condition where said needle guard is in said distal position on said needle; and a trigger articulated to said hub at a location proximally of said hinged arm, said trigger including a cam surface spaced from said hub and slidably engaged with said hinged arm such that articulation of said trigger toward said hinged arm urges said hinged arm into said extended condition and said needle guard into said distal position on said needle.

2. The shieldable needle assembly of claim 1, wherein said hinged arm includes a proximal segment articulated to said hub and a distal segment articulated to said needle guard, said proximal and distal segments of said hinged arm being articulated to one another, said cam surface of said trigger being slidably engaged primarily with said proximal segment of said hinged arm.

3. The shieldable needle assembly of claim 1, wherein said trigger includes a proximal face having a non-planar surface configuration for facilitating exertion of digital pressure thereon.

4. The shieldable needle assembly of claim 1, wherein said cam surfaces comprises a convex edge at a location on said trigger remote from the articulation of said trigger to said hub.

5. The shieldable needle assembly of claim 1, wherein said hub includes opposed proximal and distal ends, said hinged arm being articulated to said distal end of said hub.

6. The shieldable needle assembly of claim 5, wherein said proximal end of said hub comprises means for threaded engagement with a luer collar, said trigger being articulated to said hub at a location between said proximal and distal ends thereof.

7. The shieldable needle assembly of claim 1, wherein said needle guard comprises a cap and a metallic clip engaged in said cap, said metallic clip being biased against said needle when said needle guard is in said proximal position, such that stored energy in said clip urges said clip over said distal end of said needle when said needle guard is in said distal position.

8. The shieldable needle assembly of claim 1, wherein at least a portion of said hinged arm is unitary with said hub.

9. The needle assembly of claim 1, wherein at least a portion of said needle guard is unitary with at least said distal segment of said hinged arm.

10. A single handedly actuatable shield assembly for a needle, said needle comprising an elongate needle cannula having opposed proximal and distal ends and a hub securely mounted around said proximal end of said needle cannula, said shield assembly comprising:

a shield hingedly connected to said hub and movable from a first condition where said distal end of said needle cannula is exposed to a second position where said distal end of said needle cannula is enclosed by said shield; and a trigger hingedly connected to said hub at a location spaced from said shield, portions of said trigger spaced from said hub being engageable with portions of said shield for urging said shield into said second position where said distal end of said needle cannula is enclosed.

11. The assembly of claim 10, wherein said shield comprises a hinged arm articulated to said hub and a needle guard connected to said hinged arm, said trigger being engageable with said hinged arm of said shield.

12. The assembly of claim 11, wherein said hinged arm comprises a proximal segment defining portions of said hinged arm articulated to said hub, said hinged arm further comprising a distal segment articulated to said proximal segment and defining portions of said hinged arm connected to said needle guard, said hinged arm being substantially collapsed in said first condition of said shield and being substantially linearly extended in said second condition of said shield.

13. The assembly of claim 12, wherein said proximal segment of said hinged arm is articulated to said guard.

14. The assembly of claim 10, wherein said trigger includes an arcuate cam edge at a location thereon spaced from the hinged connection of said trigger to said hub, said arcuate cam edge defining portions of said trigger that are slidably engageable with said shield.

15. The assembly of claim 14, wherein said trigger includes an actuating surface having surface irregularities for facilitating digital manipulation, said actuating surface facing away from said needle cannula.

* * * * *